United States Patent [19]
Meyer et al.

[11] Patent Number: 5,154,753
[45] Date of Patent: Oct. 13, 1992

[54] CYCLOHEXENONE DEIVATIVES, THEIR PREPARATION AND THEIR USE AS HERBICIDES AND PLANT GROWTH REGULATORS

[75] Inventors: Norbert Meyer, Ladenburg; Johann Jung; Wilhelm Rademacher, both of Limburgerhof; Dieter Kolassa, Ludwigshafen; Rainer Becker, Bad Duerkheim; Dieter Jahn, Edingen-Neckarhausen; Michael Keil, Freinsheim; Ulrich Schirmer, Heidelberg; Bruno Wuerzer, Otterstadt, all of Fed. Rep. of Germany

[73] Assignee: BASF Aktiengesellschaft, Ludwigshafen, Fed. Rep. of Germany

[21] Appl. No.: 746,804

[22] Filed: Aug. 14, 1991

Related U.S. Application Data

[63] Continuation of Ser. No. 530,459, May 30, 1990, abandoned, which is a continuation of Ser. No. 262,096, Oct. 19, 1988, abandoned, which is a continuation of Ser. No. 939,032, Dec. 8, 1986, abandoned.

[30] Foreign Application Priority Data

Dec. 9, 1985 [DE] Fed. Rep. of Germany ....... 3543447

[51] Int. Cl.$^5$ ............................................ A01N 33/24
[52] U.S. Cl. ..................... 71/121; 558/430; 560/118; 564/257; 568/43; 568/367; 71/98; 71/105; 71/106; 71/122
[58] Field of Search ........................ 558/430; 560/118; 564/257; 568/43, 307; 71/98, 105, 106, 121, 122

[56] References Cited

U.S. PATENT DOCUMENTS

| | | | |
|---|---|---|---|
| 4,249,937 | 2/1981 | Iwataki et al. | 71/121 |
| 4,639,267 | 1/1987 | Farguharson et al. | 71/121 |
| 4,640,708 | 2/1987 | Bird et al. | 71/121 |
| 4,666,510 | 5/1987 | Watson et al. | 564/256 |
| 4,717,418 | 1/1988 | Warner et al. | 71/121 |
| 4,740,237 | 4/1988 | Jahn et al. | 564/257 |

FOREIGN PATENT DOCUMENTS

| | | | |
|---|---|---|---|
| 1196657 | 11/1985 | Canada | 71/121 |
| 0123001 | 10/1984 | European Pat. Off. | 71/121 |
| 0126713 | 11/1984 | European Pat. Off. | 71/121 |
| 0071707 | 12/1984 | European Pat. Off. | 71/121 |

*Primary Examiner*—James H. Reamer
*Attorney, Agent, or Firm*—Keil & Weinkauf

[57] ABSTRACT

Cyclohexenone derivatives of the formula

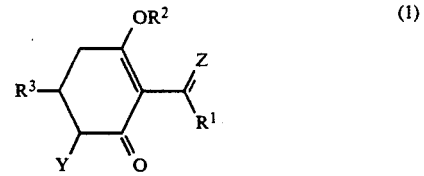

(1)

where $R^1$, $R^2$, $R^3$, Y and Z have the meanings given in the disclosure, processes for their manufacture, herbicidal and growth-regulating agents containing the novel active ingredients, and processes for combating unwanted plant growth and for regulating plant growth.

9 Claims, No Drawings

CYCLOHEXENONE DEIVATIVES, THEIR PREPARATION AND THEIR USE AS HERBICIDES AND PLANT GROWTH REGULATORS

This application is a continuation of application Ser. No. 530,459, filed on May 30, 1990 now abandoned which is a continuation of Ser. No. 262,096, now abandoned filed on Oct. 19, 1988, which is a continuation of Ser. No. 939,032 filed on Dec. 8, 1986 now abandoned.

The present invention relates to novel cyclohexenone derivatives, a process for their preparation, herbicides and plant growth regulators which contain the novel active ingredients and methods for controlling undesirable plant growth and regulating plant growth.

The herbicidal action of cyclohexenone oxime ether derivatives which possess a substituted cycloalkyl radical in the 5-position has been disclosed (DE-A-2 119 940).

It has also been disclosed that certain 2-acyl-3-hydroxy-2-cyclohexen-1-ones regulate plant growth (EP-A-123 001 and EP-A-126 713).

We have found novel cyclohexenone derivatives of the formula I

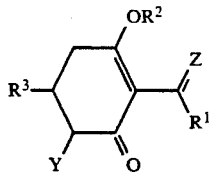

where
- $R^1$ is $C_1$–$C_4$-alkyl,
- $R^2$ is hydrogen, $C_1$–$C_{20}$-alkylcarbonyl, $C_2$–$C_{20}$-alkenylcarbonyl, in particular those having one C—C double bond, or benzoyl which is unsubstituted or substituted in the phenyl ring by $C_1$–$C_8$-alkyl, or is $C_1$–$C_4$-trialkylsilyl, $C_1$–$C_7$-alkylsulfonyl, arylsulfonyl, $C_1$–$C_4$-dialkylphosphono or $C_1$–$C_4$-dialkylthiophosphono,
- $R^3$ is a nonaromatic 5-membered to 12-membered carbocyclic structure or carbobicyclic structure which contains 3 methyl groups and 1 or 2 substituents selected from the group consisting of hydroxyl, $C_1$–$C_4$-alkylcarbonyloxy, $C_1$–$C_4$-alkylcarbonylthio, carboxymethylthio, $C_1$–$C_4$-alkoxycarbonylmethylthio, $C_1$–$C_4$-alkyl-carbamoyloxy, $C_1$–$C_4$-dialkylcarbamoyloxy, $C_1$–$C_4$-alkanoylamino, $C_3$–$C_6$-cycloalkylcarbonylamino, $C_1$–$C_4$-alkoxy, aryloxy, $C_1$–$C_4$-alkylthio, arylthio, $C_3$- or $C_4$-alkoxyalkyl, $C_1$–$C_3$-dialkylamino, $C_1$–$C_4$-alkylsulfonyloxy, $C_1$–$C_4$-alkylsulfinyloxy, $C_1$–$C_4$-trialkylsilyl, $C_1$–$C_4$-dialkylphosphono, dimethoxymethyl, 1,3-dioxolan-2-yl, 1,3-dithiolan-2-yl, halogen, mercapto, $C_1$–$C_4$-alkylthiocarbonyl, $C_1$–$C_4$-alkoxycarbonyl, N-($C_1$–$C_4$-alkyl)-carbamoyl or carboxyl,
- Y is hydrogen, methoxycarbonyl, cyano, $C_1$–$C_4$-alkyl or halogen and
- Z is oxygen or a radical $NOR^4$, where $R^4$ is $C_1$–$C_4$-alkyl, $C_3$- or $C_4$-alkenyl, $C_3$- or $C_4$-alkynyl, $C_2$–$C_4$-haloalkyl, $C_2$–$C_4$-haloalkenyl, in particular those having 1, 2 or 3 halogen atoms, or $C_2$–$C_4$-alkoxyalkyl, and salts of the compounds in which $R^2$ is hydrogen, with the proviso that $R^3$ is not cyclohexyl which is substituted by $C_1$–$C_4$-alkoxy, chlorine or bromine.

The novel cyclohexenone derivatives of the formula I where Z is a radical $NOR^4$ have a good herbicidal action, preferentially against species from the grass family (Gramineae).

Cyclohexenone derivatives of the formula I in which Z is oxygen possess advantageous growth-regulating properties.

The compounds of the formula I can occur in a plurality of tautomeric forms, all of which are embraced by the claim. For example, the compounds in which $R^2$ is hydrogen and Z is $NOR^4$ can occur, inter alia, in the following tautomeric forms:

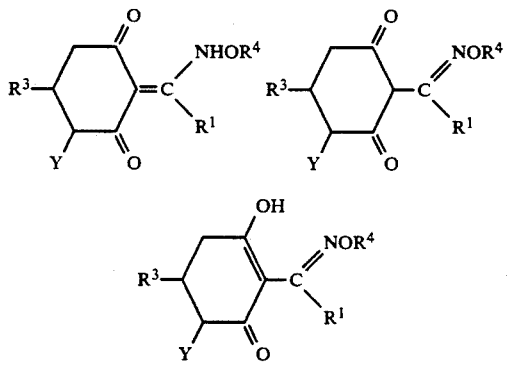

Where $R^4$ is $C_2$–$C_4$-haloalkyl or -alkenyl, these radicals should possess 1, 2 or 3 halogen atoms. Furthermore, where $R^4$ is $C_3$- or $C_4$-alkenyl or $C_2$–$C_4$-haloalkenyl, both isomers are embraced by the claim in the case of those radicals in which E and Z isomers can occur.

In formula I, $R^1$ is, for example, methyl, ethyl, propyl, isopropyl, butyl, sec-butyl, isobutyl or tertbutyl.

In formula I, $R^2$ is, for example, hydrogen, acetyl, propionyl, acroyl, butyryl, isobutyryl, pivaloyl, valeroyl, 2-ethylhexanoyl, caproyl, caprinoyl, lauroyl, palmitoyl, stearoyl, oleoyl, benzoyl, 4-methylbenzoyl, 4-hexylbenzoyl, trimethylsilyl, triethylsilyl, methylsulfonyl, ethylsulfonyl, benzoylsulfonyl, 4-methylphenylsulfonyl, 2-methylphenylsulfonyl, 2-chlorophenylsulfonyl, 4-chlorophenylsulfonyl, diethylphosphono or diethylthiophosphono.

The basic structures of the carbocyclic ring systems of $R^3$ in formula I are, for example, the cyclopentane, cyclohexane, cycloheptane or cyclooctane ring.

$R^3$ is, for example, a cyclohexyl ring which may carry the following substituents: 3,4-dihydroxy, 3,4-diacetoxy, 3,4-dibutyryloxy, 3-acetoxy-4-hydroxy-4-methyl, 3,4-dihydroxy-4-methyl, 3-acetylamino, 3,4-dibenzoyloxy, 3-benzoyloxy-4-hydroxy-4-methyl, 3,4-bis(methylcarbamoyloxy), 3-butyryloxy-4-hydroxy-4-methyl, 3-benzoyloxy-4-hydroxy-4-methyl, 3-dimethylamino-4-hydroxy-4-methylcyclohexyl, 4-hydroxy-4-methyl-3-methylthio, 3-acetylthio-4-hydroxy-4-methyl, 4-hydroxy-4-methyl-3-methylthiocarbonyl, 3-acetylthio-4-methyl, 4-acetylthio, 4-methylthiocarbonyl, 4-mercapto, 3-mercapto-4-methyl, 2-methylthio, 3-methylthio, 3-hexylthio, 4-methylthio, 4-phenylthio, 3-phenylthio, 4-trimethylsilyl, 3-trimethylsilyl, 4-diethylphosphono, 4-methylsulfonyloxy, 4-acetoxy, 4-benzoyloxy, 4-hydroxy, 4-carboxymethylthio, 4-acetylamino, 4-cyclopropylcarbonylamino, 4-carboxyl, 4-methoxycarbonyl, 4-methylcarbamoyloxy, 4-(1,3- dioxolan-2-yl), 4-dimethoxymethyl, 4-(1,3-dithiixan-2-yl), 4-methoxymethoxy, 4-methoxyethoxy, 3-chloro, 3-methoxymethyl-5-methyl, 5-methoxymethyl-2-methyl or 3-ethylthio-4-hydroxy-4-methyl.

Other examples of $R^3$ are 2-methoxymethyl-5-methylcyclohexenyl, 5-methoxymethyl-2-methylcyclohexenyl, 4,5-dihydroxycyclooctyl and 4,5-diacetoxycyclooctyl.

If, in formula I, Z is $NOR^4$, $R^4$ is, for example, methyl, ethyl, propyl, allyl, (E)-but-2-en-1-yl, propargyl, 2-chloroethyl, (E)-3-chloropropen-1-yl, methoxymethyl or 2-methoxyethyl.

Suitable salts of the compounds of the formula I, in which $R^2$ is hydrogen, are salts which can be used in agriculture, for example the alkali metal salts, in particular the potassium or sodium salts, alkaline earth metal salts, in particular calcium and magnesium salts, manganese, copper, zinc or iron salts and ammonium, sulfonium, sulfoxonium and phosphonium salts, for example ammonium, tetraalkylammonium, benzyltrialkylammonium, trialkylsulfonium or trialkylsulfoxonium salts.

Cyclohexenone derivatives of the formula I in which $R^1$ is $C_2$- or $C_3$-alkyl are preferred.

The cyclohexenone derivatives of the formula I where Z is $NOR^4$ can be obtained by reacting those cyclohexenone derivatives of the formula I in which Z is oxygen with an ammonium compound of the formula $R^4$—O—$NH_3Y$, in which $R^4$ has the above meanings and Y is an anion (e.g. chloride, bromide or sulfate).

The reaction is advantageously carried out in the heterogeneous phase in an inert diluent at from 0° to 80° C. or from 0° C. to the boiling point of the reaction mixture, in the presence of a base. Examples of suitable bases are carbonates, bicarbonates, acetates, alcoholates, hydroxides and oxides of alkali metals and alkaline earth metals, in particular of sodium, potassium, magnesium or calcium. Organic bases, such as pyridine or tertiary amines, may also be used. The base is added, for example, in an amount of from 0.5 to 2 moles, based on the ammonium compound.

Examples of suitable solvents are dimethyl sulfoxide, alcohols, such as methanol, ethanol or isopropanol, benzene, hydrocarbons and chlorohydrocarbons, such as chloroform, dichloroethane, hexane or cyclohexane, esters, such as ethyl acetate, and ethers, such as dioxane or tetrahydrofuran.

The reaction is complete after a few hours, and the reaction product can then be isolated by evaporating down the mixture, adding water and extracting with a nonpolar solvent, such as methylene chloride, and distilling off the solvent under reduced pressure.

The compounds of the formula I (where Z is $NOR^4$) may furthermore be obtained by reacting a compound of the formula I (where Z is oxygen) with a hydroxylamine of the formula $R^4O$—$NH_2$, in which $R^4$ has the above meanings, in an inert diluent at from 0° to 80° C., in particular from 15° to 70° C. If necessary, the hydroxylamine may be employed in the form of an aqueous solution.

Examples of suitable solvents for this reaction are alcohols, such as methanol, ethanol, isopropanol or cyclohexanol, hydrocarbons and chlorohydrocarbons, such as hexane, cyclohexane, methylene chloride, toluene or dichloroethane, esters, such as ethyl acetate, nitriles, such as acetonitrile, and cyclic ethers, such as tetrahydrofuran.

The alkali metal salts of the compounds of the formula I (where Z is $NOR^4$) can be obtained by treating these compounds with sodium hydroxide or potassium hydroxide in aqueous solution or in an organic solvent, such as methanol, ethanol or acetone. Sodium alcoholates and potassium alcoholates may also be used as bases.

The other metal salts, for example the manganese, copper, zinc, iron, calcium, magnesium and barium salts, can be prepared from the sodium salts by reaction with the corresponding metal chlorides in aqueous solution. The ammonium, sulfonium, sulfoxonium and phosphonium salts can be prepared from the compounds of the formula I using ammonium, sulfonium, sulfoxonium or phosphonium hydroxides, if necessary in aqueous solution.

The cyclohexenone derivatives of the formula I in which Z is oxygen are obtained via the enol-ester intermediate. The cyclohexenone derivative of the formula II

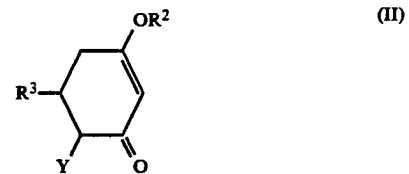

where $R^2$, $R^3$ and Y have the above meanings, is reacted with an acid chloride of the formula $R^1$—COCL, in which $R^1$ has the above meanings, in the presence of a base (e.g. triethylamine) in an inert diluent (e.g. tetrahydrofuran), and the product is then treated with an imidazole or pyridine derivative (e.g. 4-(N,N-dimethylamino)-pyridine). This process step is known per se and is described in JP-A-63052/1979.

However, it is also possible to use other conventional methods, such as those described in, for example, Tetrahedron Lett. 29, (1975), 2491.

The compounds of the formula I are obtained by conventional methods, as is evident from the scheme below:

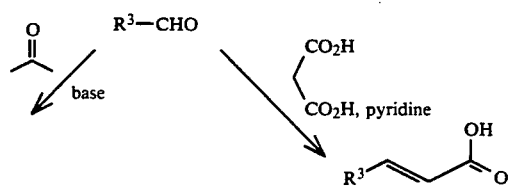

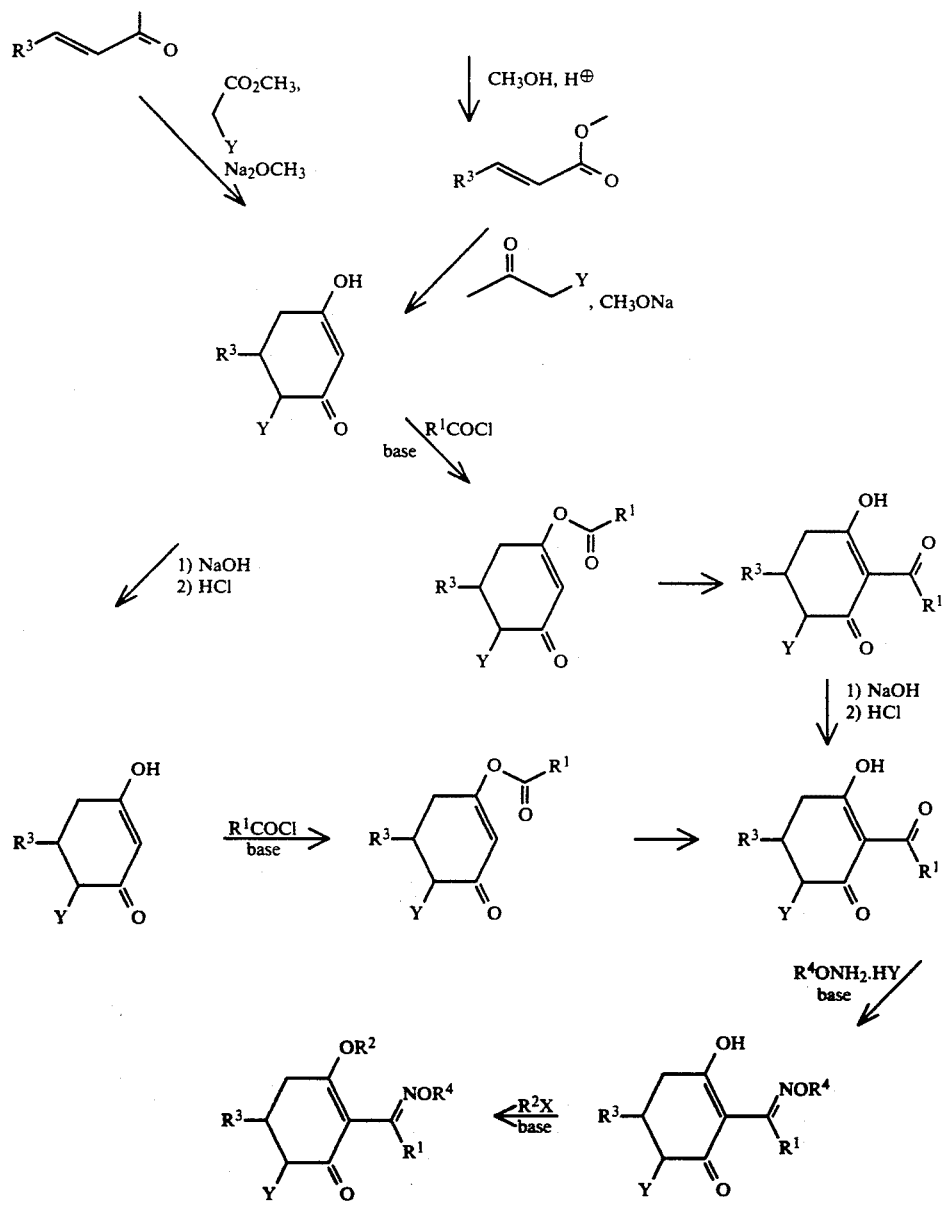

(The open-chain, alpha, beta-unsaturated ketone shown in the scheme, and the unsaturated carboxylic acid, can occur both as the cis isomer and as the trans isomer.)

Aldehydes of the general formula $R^3$—CHO are obtained by methods known from the literature, for example by oxidation of alcohols, reduction of carboxylic acid derivatives or hydroformylation of olefins.

The functional group or groups in the cyclohexyl radical can be introduced at any stage of the synthesis, but is preferably introduced at the stage of compounds of the type described by formula I (where A is oxygen). All methods known from the literature are suitable for this purpose, for example addition at a double bond, nucleophilic ring cleavage of oxiranes or nucleophilic substitution reactions.

The Examples which follow illustrate the preparation of the cyclohexenone derivatives. In the Examples, parts by weight bear the same relation to parts by volume as that of the kilogram to the liter.

EXAMPLE A 30 parts by weight of 2-butyryl-5-(3,4-epoxycyclohexyl)-3-hydroxy-2-cyclohexen-1-one and 130 parts by volume of 10% strength by weight sodium hydroxide solution were stirred at room temperature until starting material was no longer detectable by thin layer chromatography. The solution was acidified with concentrated hydrochloric acid and extracted with dichloromethane. The organic phase was dried over sodium sulfate, and the solvent was distilled off under reduced pressure. The residue was purified by column chromatography (silica gel, 230–400 mesh, 200:1 dichloromethane/methanol mixture). 26 parts by weight (81%) of 2-butyryl-5-(3,4-dihydroxycyclohexyl)-3-hydroxy-2-cyclohexen-1-one (compound No. 378) were obtained as a yellow oil.

EXAMPLE B 4.4 parts by weight of 2-butyryl-5-(3,4-dihydroxycyclohexyl)-3-hydroxy-2-cyclohexen-1-one, 1.6 parts by weight of ethoxyamine, 1.4 parts by weight of sodium bicarbonate and 60 parts by volume of methanol were stirred for 16 hours at room temperature. The solvent was distilled off under reduced pressure, 50 parts by volume of water and 50 parts by volume of dichloromethane were added to the remaining residue and the mixture was stirred vigorously, after which the phases were separated and the organic phase was dried over sodium sulfate. After the solvent had been distilled off under reduced pressure, 4.5 parts by weight (89%) of 5-(3,4-dihydroxycyclohexyl)-2-(1-ethoxyiminopropyl)-3-hydroxy-2-cyclohexen-1-one (compound No. 5) were obtained.

The compounds of the formula I (where Z is NOR$^4$) which are listed in Table 1 can be prepared in a similar manner.

The $^1$H NMR spectra were recorded in deuterochloroform or hexadeuterodimethyl sulfoxide as the solvent, using tetramethylsilane as the internal standard. The chemical shifts are recorded as δ[ppm]. The multiplicities are stated as follows: s=singlet, d=doublet, t=triplet, q=quartet and m=multiplet.

TABLE 1

| Compound no. | R$^3$ | R$^2$ | R$^1$ | R$^4$ | Y | $^1$H-NMR data |
|---|---|---|---|---|---|---|
| 1 | 3,4-dihydroxycyclohexyl | H | ethyl | ethyl | H | 1.3(t, 3H), 2.6(m), 4.1(q, 2H) |
| 2 | 3,4-dihydroxycyclohexyl | H | ethyl | allyl | H | 1.1(t, 3H), 2.9(q), 4.55(d) |
| 3 | 3,4-dihydroxycyclohexyl | H | ethyl | (E)-2-butenyl | H | 1.7(d), 2.9(q), 4.45(d) |
| 4 | 3,4-dihydroxycyclohexyl | H | ethyl | (E)-3-chloro-2-propenyl | H | 2.9(q), 3.55(m), 3.7(m) |
| 5 | 3,4-dihydroxycyclohexyl | H | propyl | ethyl | H | 1.3(t, 3H), 2.6(t, 2H), 4.05 (q, 2H) |
| 6 | 3,4-dihydroxycyclohexyl | H | propyl | allyl | H | 2.9(t, 2H), 3.6(m), 3.7(m), 5.3(m) |
| 7 | 3,4-dihydroxycyclohexyl | H | propyl | (E)-2-butenyl | H | 0.95(t), 2.6(t), 4.45(d) |
| 8 | 3,4-dihydroxycyclohexyl | H | propyl | (E)-3-chloro-2-propenyl | H | 0.95(t, 3H), 2.85(t, 2H), 4.55(d) |
| 9 | 3,4-diacetoxycyclohexyl | H | ethyl | ethyl | H | 1.1(t), 2.1(s), 2.9(t) |
| 10 | 3,4-diacetoxycyclohexyl | H | ethyl | allyl | H | |
| 11 | 3,4-diacetoxycyclohexyl | H | ethyl | (E)-2-butenyl | H | |
| 12 | 3,4-diacetoxycyclohexyl | H | ethyl | (E)-3-chloro-2-propenyl | H | 1.6(m), 2.1(s), 4.9(m) |
| 13 | 3,4-diacetoxycyclohexyl | H | propyl | ethyl | H | 2.1(s), 4.15(q), 4.9(s), 5.0(s) |
| 14 | 3,4-diacetoxycyclohexyl | H | propyl | allyl | H | 1.0(m), 2.1(s), 4.55(d) |
| 15 | 3,4-diacetoxycyclohexyl | H | propyl | (E)-2-butenyl | H | 1.0(t), 4.5(d), 5.7(m) |
| 16 | 3,4-diacetoxycyclohexyl | H | propyl | (E)-3-chloro-2-propenyl | H | 2.1(s), 4.55(d), 4.9(s), 5,0(s) |
| 17 | 3,4-dibutyryloxycyclohexyl | H | ethyl | ethyl | H | |
| 18 | 3,4-dibutyryloxycyclohexyl | H | ethyl | allyl | H | |
| 19 | 3,4-dibutyryloxycyclohexyl | H | ethyl | (E)-2-butyl | H | |
| 20 | 3,4-dibutyryloxycyclohexyl | H | ethyl | (E)-3-chloro-2-propenyl | H | 1.6(m), 2.1(s), 4.9(m) |
| 21 | 3,4-dibutyryloxycyclohexyl | H | propyl | ethyl | H | 1.3(t), 2.3(H), 4.9(m), 5.0(m) |
| 22 | 3,4-dibutyryloxycyclohexyl | H | propyl | allyl | H | 1.7(m), 2.3(t), 5.35(m) |
| 23 | 3,4-dibutyryloxycyclohexyl | H | propyl | (E)-2-butyl | H | |
| 24 | 3,4-dibutyryloxycyclohexyl | H | propyl | (E)-3-chloro-2-propenyl | H | 1.0(t), 2.9(m), 4.5(d) |
| 25 | 3-acetoxy-4-hydroxy-4-methylcyclohexyl | H | ethyl | ethyl | H | |
| 26 | 3-acetoxy-4-hydroxy-4-methylcyclohexyl | H | ethyl | allyl | H | |
| 27 | 3-acetoxy-4-hydroxy-4-methylcyclohexyl | H | ethyl | (E)-2-butyl | H | |
| 28 | 3-acetoxy-4-hydroxy-4-methylcyclohexyl | H | ethyl | (E)-3-chloro-2-propenyl | H | |
| 29 | 3-acetoxy-4-hydroxy-4-methylcyclohexyl | H | propyl | ethyl | H | 1.2(s), 2.1(s), 4.8(s) |
| 30 | 3-acetoxy-4-hydroxy-4-methylcyclohexyl | H | propyl | allyl | H | |
| 31 | 3-acetoxy-4-hydroxy-4-methylcyclohexyl | H | propyl | (E)-2-butenyl | H | |
| 32 | 3-acetoxy-4-hydroxy-4-methylcyclohexyl | H | propyl | (E)-3-chloro-2-propenyl | H | 2.1(s), 4.5(d), 6.35(d) |
| 33 | 3,4-dihydroxy-4-methyl-cyclohexyl | H | ethyl | ethyl | H | |
| 34 | 3,4-dihydroxy-4-methyl-cyclohexyl | H | ethyl | allyl | H | |
| 35 | 3,4-dihydroxy-4-methyl-cyclohexyl | H | ethyl | (E)-2-butenyl | H | |
| 36 | 3,4-dihydroxy-4-methyl-cyclohexyl | H | ethyl | (E)-3-chloro-2-propenyl | H | |
| 37 | 3,4-dihydroxy-4-methyl-cyclohexyl | H | propyl | ethyl | H | 1.3(m), 3.6(m), 4.1(q) |
| 38 | 3,4-dihydroxy-4-methyl-cyclohexyl | H | propyl | allyl | H | |
| 39 | 3,4-dihydroxy-4-methyl-cyclohexyl | H | propyl | (E)-2-butenyl | H | |
| 40 | 3,4-dihydroxy-4-methyl-cyclohexyl | H | propyl | (E)-3-chloro-2-propenyl | H | |
| 41 | 3-acetylaminocyclohexyl | H | ethyl | ethyl | H | |
| 42 | 3-acetylaminocyclohexyl | H | ethyl | allyl | H | |
| 43 | 3-acetylaminocyclohexyl | H | ethyl | (E)-2-butenyl | H | |
| 44 | 3-acetylaminocyclohexyl | H | ethyl | (E)-3-chloro-2-propenyl | H | |
| 45 | 3-acetylaminocyclohexyl | H | propyl | ethyl | H | 0.95(t, 3H), 1.9(s, 3H), 4.0(q, 2H) |
| 46 | 3-acetylaminocyclohexyl | H | propyl | allyl | H | |
| 47 | 3-acetylaminocyclohexyl | H | propyl | (E)-2-butenyl | H | |
| 48 | 3-acetylaminocyclohexyl | H | propyl | (E)-3-chloro-2-propenyl | H | |

TABLE 1-continued

| Compound no. | R³ | R² | R¹ | R⁴ | Y | ¹H-NMR data |
|---|---|---|---|---|---|---|
| 49 | 3,4-dibenzoyloxycyclohexyl | H | ethyl | ethyl | H | |
| 50 | 3,4-dibenzoyloxycyclohexyl | H | ethyl | allyl | H | |
| 51 | 3,4-dibenzoyloxycyclohexyl | H | ethyl | (E)-2-buten-1-yl | H | |
| 52 | 3,4-dibenzoyloxycyclohexyl | H | ethyl | (E)-3-chloro-2-propenyl | H | |
| 53 | 3,4-dibenzoyloxycyclohexyl | H | propyl | ethyl | H | |
| 54 | 3,4-dibenzoyloxycyclohexyl | H | propyl | allyl | H | |
| 55 | 3,4-dibenzoyloxycyclohexyl | H | propyl | (E)-2-butenyl | H | |
| 56 | 3,4-dibenzoyloxycyclohexyl | H | propyl | (E)-3-chloro-2-propenyl | H | |
| 57 | 3-benzoyloxy-4-hydroxy-4-methylcyclohexyl | H | ethyl | ethyl | H | |
| 58 | 3-benzoyloxy-4-hydroxy-4-methylcyclohexyl | H | ethyl | allyl | H | |
| 59 | 3-benzoyloxy-4-hydroxy-4-methylcyclohexyl | H | ethyl | (E)-2-butenyl | H | |
| 60 | 3-benzoyloxy-4-hydroxy-4-methylcyclohexyl | H | ethyl | (E)-3-chloro-2-propenyl | H | |
| 61 | 3-benzoyloxy-4-hydroxy-4-methylcyclohexyl | H | propyl | ethyl | H | 0.97(t), 1.30(s), 2.91(t) |
| 62 | 3-benzoyloxy-4-hydroxy-4-methylcyclohexyl | H | propyl | allyl | H | |
| 63 | 3-benzoyloxy-4-hydroxy-4-methylcyclohexyl | H | propyl | (E)-2-butenyl | H | |
| 64 | 3-benzoyloxy-4-hydroxy-4-methylcyclohexyl | H | propyl | (E)-3-chloro-2-propenyl | H | |
| 65 | 3,4-bis(methylcarbamoyloxy)-cyclohexyl | H | ethyl | ethyl | H | |
| 66 | 3,4-bis(methylcarbamoyloxy)-cyclohexyl | H | ethyl | allyl | H | |
| 67 | 3,4-bis(methylcarbamoyloxy)-cyclohexyl | H | ethyl | (E)-2-butenyl | H | |
| 68 | 3,4-bis(methylcarbamoyloxy)-cyclohexyl | H | ethyl | (E)-3-chloro-2-propenyl | H | |
| 69 | 3,4-bis(methylcarbamoyloxy)-cyclohexyl | H | propyl | ethyl | H | 1.3(t), 2.8(d), 4.1(q) |
| 70 | 3,4-bis(methylcarbamoyloxy)-cyclohexyl | H | propyl | allyl | H | 2.8(d), 4.5(d), 5.4(m) |
| 71 | 3,4-bis(methylcarbamoyloxy)-cyclohexyl | H | propyl | (E)-2-butenyl | H | 0.9(t), 2.8(d), 4.5(d) |
| 72 | 3,4-bis(methylcarbamoyloxy)-cyclohexyl | H | propyl | (E)-3-chloro-2-propenyl | H | 0.96(t), 2.8(d), 6.3(d) |
| 73 | 3-butyryloxy-4-hydroxy-4-methylcyclohexyl | H | ethyl | ethyl | H | |
| 74 | 3-butyryloxy-4-hydroxy-4-methylcyclohexyl | H | ethyl | allyl | H | |
| 75 | 3-butyryloxy-4-hydroxy-4-methylcyclohexyl | H | ethyl | (E)-2-butenyl | H | |
| 76 | 3-butyryloxy-4-hydroxy-4-methylcyclohexyl | H | ethyl | (E)-3-chloro-2-propenyl | H | |
| 77 | 3-butyryloxy-4-hydroxy-4-methylcyclohexyl | H | propyl | ethyl | H | |
| 78 | 3-butyryloxy-4-hydroxy-4-methylcyclohexyl | H | propyl | allyl | H | |
| 79 | 3-butyryloxy-4-hydroxy-4-methylcyclohexyl | H | propyl | (E)-butenyl | H | |
| 80 | 3-butyryloxy-4-hydroxy-4-methylcyclohexyl | H | propyl | (E)-3-chloro-2-propenyl | H | |
| 81 | 3-benzoyloxy-4-hydroxy-4-methylcyclohexyl | H | ethyl | ethyl | H | |
| 82 | 3-benzoyloxy-4-hydroxy-4-methylcyclohexyl | H | ethyl | allyl | H | |
| 83 | 3-benzoyloxy-4-hydroxy-4-methylcyclohexyl | H | ethyl | (E)-2-butenyl | H | |
| 84 | 3-benzoyloxy-4-hydroxy-4-methylcyclohexyl | H | ethyl | (E)-3-chloro-2-propenyl | H | |
| 85 | 3-benzoyloxy-4-hydroxy-4-methylcyclohexyl | H | propyl | ethyl | H | |
| 86 | 3-benzoyloxy-4-hydroxy-4-methylcyclohexyl | H | propyl | allyl | H | |
| 87 | 3-benzoyloxy-4-hydroxy-4-methylcyclohexyl | H | propyl | (E)-2-butenyl | H | |
| 88 | 3-benzoyloxy-4-hydroxy-4-methylcyclohexyl | H | propyl | (E)-3-chloro-2-propenyl | H | |
| 89 | 4-hydroxy-4-methyl-3-methylthiocyclohexyl | H | ethyl | ethyl | H | |
| 90 | 4-hydroxy-4-methyl-3-methyl-thiocyclohexyl | H | ethyl | allyl | H | |
| 91 | 4-hydroxy-4-methyl-3-methyl-thiocyclohexyl | H | ethyl | (E)-2-butenyl | H | |
| 92 | 4-hydroxy-4-methyl-3-methyl-thiocyclohexyl | H | ethyl | (E)-3-chloro-2-propenyl | H | |

TABLE 1-continued

| Compound no. | R³ | R² | R¹ | R⁴ | Y | ¹H-NMR data |
|---|---|---|---|---|---|---|
| 93 | 4-hydroxy-4-methyl-3-methyl-thiocyclohexyl | H | propyl | ethyl | H | |
| 94 | 4-hydroxy-4-methyl-3-methylthiocyclohexyl | H | propyl | allyl | H | |
| 95 | 4-hydroxy-4-methyl-3-methylthiocyclohexyl | H | propyl | (E)-2-butenyl | H | |
| 96 | 4-hydroxy-4-methyl-3-methylthiocyclohexyl | H | propyl | (E)-3-chloro-2-propenyl | H | |
| 97 | 3-acetylthio-4-hydroxy-4-methylcyclohexyl | H | ethyl | ethyl | H | |
| 98 | 3-acetylthio-4-hydroxy-4-methylcyclohexyl | H | ethyl | allyl | H | |
| 99 | 3-acetylthio-4-hydroxy-4-methylcyclohexyl | H | ethyl | (E)-2-butenyl | H | |
| 100 | 3-acetylthio-4-hydroxy-4-methylcyclohexyl | H | ethyl | (E)-3-chloro-2-propenyl | H | |
| 101 | 3-acetylthio-4-hydroxy-4-methylcyclohexyl | H | propyl | ethyl | H | 1.28(s), 2.35(s), 4.09(q) |
| 102 | 3-acetylthio-4-hydroxy-4-methylcyclohexyl | H | propyl | allyl | H | |
| 103 | 3-acetylthio-4-hydroxy-4-methylcyclohexyl | H | propyl | (E)-2-butenyl | H | |
| 104 | 3-acetylthio-4-hydroxy-4-methylcyclohexyl | H | propyl | (E)-3-chloro-2-propenyl | H | |
| 105 | 4-hydroxy-4-methyl-3-methylthiocarbonylcyclohexyl | H | ethyl | ethyl | H | |
| 106 | 4-hydroxy-4-methyl-3-methylthiocarbonylcyclohexyl | H | ethyl | allyl | H | |
| 107 | 4-hydroxy-4-methyl-3-methylthiocarbonylcyclohexyl | H | ethyl | (E)-2-butenyl | H | |
| 108 | 4-hydroxy-4-methyl-3-methylthiocarbonylcyclohexyl | H | ethyl | (E)-3-chloro-2-propenyl | H | |
| 109 | 4-hydroxy-4-methyl-3-methylthiocarbonylcyclohexyl | H | propyl | ethyl | H | 0.96(t), 1.37(s), 4.10(q) |
| 110 | 4-hydroxy-4-methyl-3-methylthiocarbonylcyclohexyl | H | propyl | allyl | H | 0.97(t), 1.38(s), 2.15(s) |
| 111 | 4-hydroxy-4-methyl-3-methylthiocarbonylcyclohexyl | H | propyl | (E)-2-butenyl | H | |
| 112 | 4-hydroxy-4-methyl-3-methylthiocarbonylcyclohexyl | H | propyl | (E)-3-chloro-2-propenyl | H | 0.95(t), 2.15(s), 4.52(d) |
| 113 | 3-acetylthio-4-methylcyclohexyl | H | ethyl | ethyl | H | |
| 114 | 3-acetylthio-4-methylcyclohexyl | H | ethyl | allyl | H | |
| 115 | 3-acetylthio-4-methylcyclohexyl | H | ethyl | (E)-2-butenyl | H | |
| 116 | 3-acetylthio-4-methylcyclohexyl | H | ethyl | (E)-3-chloro-2-propenyl | H | |
| 117 | 3-acetylthio-4-methylcyclohexyl | H | propyl | ethyl | H | 2.37(s), 3.98(s), 4.11(q) |
| 118 | 3-acetylthio-4-methylcyclohexyl | H | propyl | allyl | H | |
| 119 | 3-acetylthio-4-methylcyclohexyl | H | propyl | (E)-2-butenyl | H | |
| 120 | 3-acetylthio-4-methylcyclohexyl | H | propyl | (E)-3-chloro-2-propenyl | H | |
| 121 | 3-dimethylamino-4-hydroxy-4-methyl-cyclohexyl | H | ethyl | ethyl | H | |
| 122 | 3-dimethylamino-4-hydroxy-4-methyl-cyclohexyl | H | ethyl | allyl | H | |
| 123 | 3-dimethylamino-4-hydroxy-4-methyl-cyclohexyl | H | ethyl | (E)-2-butenyl | H | |
| 124 | 3-dimethylamino-4-hydroxy-4-methyl-cyclohexyl | H | ethyl | (E)-3-chloro-2-propenyl | H | |
| 125 | 3-dimethylamino-4-hydroxy-4-methyl-cyclohexyl | H | propyl | ethyl | H | |
| 126 | 3-dimethylamino-4-hydroxy-4-methyl-cyclohexyl | H | propyl | allyl | H | |
| 127 | 3-dimethylamino-4-hydroxy-4-methyl-cyclohexyl | H | propyl | (E)-2-butenyl | H | |
| 128 | 3-dimethylamino-4-hydroxy-4-methyl-cyclohexyl | H | propyl | (E)-3-chloro-2-propenyl | H | |
| 129 | 4-acetylthiocyclohexyl | H | ethyl | ethyl | H | |
| 130 | 4-acetylthiocyclohexyl | H | ethyl | allyl | H | |
| 131 | 4-acetylthiocyclohexyl | H | ethyl | (E)-2-butenyl | H | |
| 132 | 4-acetylthiocyclohexyl | H | ethyl | (E)-3-chloro-2-propenyl | H | |
| 133 | 4-acetylthiocyclohexyl | H | propyl | ethyl | H | 1.0(t), 2.3(s), 4.1(q) |
| 134 | 4-acetylthiocyclohexyl | H | propyl | allyl | H | |
| 135 | 4-acetylthiocyclohexyl | H | propyl | (E)-2-butenyl | H | |
| 136 | 4-acetylthiocyclohexyl | H | propyl | (E)-3-chloro-2-propenyl | H | |

TABLE 1-continued

| Compound no. | R³ | R² | R¹ | R⁴ | Y | ¹H-NMR data |
|---|---|---|---|---|---|---|
| 137 | 4-methylthiocarbonylcyclohexyl | H | ethyl | ethyl | H | |
| 138 | 4-methylthiocarbonylcyclohexyl | H | ethyl | allyl | H | |
| 139 | 4-methylthiocarbonylcyclohexyl | H | ethyl | (E)-2-butenyl | H | |
| 140 | 4-methylthiocarbonylcyclohexyl | H | ethyl | (E)-3-chloro-2-propenyl | H | |
| 141 | 4-methylthiocarbonylcyclohexyl | H | propyl | ethyl | H | |
| 142 | 4-methylthiocarbonylcyclohexyl | H | propyl | allyl | H | |
| 143 | 4-methylthiocarbonylcyclohexyl | H | propyl | (E)-2-butenyl | H | |
| 144 | 4-methylthiocarbonylcyclohexyl | H | propyl | (E)-3-chloro-2-propenyl | H | |
| 145 | 4-mercaptocyclohexyl | H | ethyl | ethyl | H | |
| 146 | 4-mercaptocyclohexyl | H | ethyl | allyl | H | |
| 147 | 4-mercaptocyclohexyl | H | ethyl | (E)-2-butenyl | H | |
| 148 | 4-mercaptocyclohexyl | H | ethyl | (E)-3-chloro-2-propenyl | H | |
| 149 | 4-mercaptocyclohexyl | H | propyl | ethyl | H | |
| 150 | 4-mercaptocyclohexyl | H | propyl | allyl | H | |
| 151 | 4-mercaptocyclohexyl | H | propyl | (E)-2-butenyl | H | |
| 152 | 4-mercaptocyclohexyl | H | propyl | (E)-3-chloro-2-propenyl | H | |
| 153 | 3-mercapto-4-methylcyclohexyl | H | ethyl | ethyl | H | |
| 154 | 3-mercapto-4-methylcyclohexyl | H | ethyl | allyl | H | 1.13(t), 2.90(q), 4.54(d) |
| 155 | 3-mercapto-4-methylcyclohexyl | H | ethyl | (E)-2-butenyl | H | |
| 156 | 3-mercapto-4-methylcyclohexyl | H | ethyl | (E)-3-chloro-2-propenyl | H | |
| 157 | 3-mercapto-4-methylcyclohexyl | H | propyl | ethyl | H | |
| 158 | 3-mercapto-4-methylcyclohexyl | H | propyl | allyl | H | |
| 159 | 3-mercapto-4-methylcyclohexyl | H | propyl | (E)-2-butenyl | H | |
| 160 | 3-mercapto-4-methylcyclohexyl | H | propyl | (E)-3-chloro-2-propenyl | H | |
| 161 | 3-methylthiocyclohexyl | H | ethyl | ethyl | H | |
| 162 | 3-methylthiocyclohexyl | H | ethyl | allyl | H | |
| 163 | 3-methylthiocyclohexyl | H | ethyl | (E)-2-butenyl | H | |
| 164 | 3-methylthiocyclohexyl | H | ethyl | (E)-3-chloro-2-propenyl | H | |
| 165 | 3-methylthiocyclohexyl | H | propyl | ethyl | H | |
| 166 | 3-methylthiocyclohexyl | H | propyl | allyl | H | |
| 167 | 3-methylthiocyclohexyl | H | propyl | (E)-2-butenyl | H | |
| 168 | 3-methylthiocyclohexyl | H | propyl | (E)-3-chloro-2-propenyl | H | |
| 169 | 4-methylthiocyclohexyl | H | ethyl | ethyl | H | |
| 170 | 4-methylthiocyclohexyl | H | ethyl | allyl | H | |
| 171 | 4-methylthiocyclohexyl | H | ethyl | (E)-2-butenyl | H | |
| 172 | 4-methylthiocyclohexyl | H | ethyl | (E)-3-chloro-2-propenyl | H | |
| 173 | 4-methylthiocyclohexyl | H | propyl | ethyl | H | |
| 174 | 4-methylthiocyclohexyl | H | propyl | allyl | H | |
| 175 | 4-methylthiocyclohexyl | H | propyl | (E)-2-butenyl | H | |
| 176 | 4-methylthiocyclohexyl | H | propyl | (E)-3-chloro-2-propenyl | H | |
| 177 | 4-butylthiocyclohexyl | H | ethyl | ethyl | H | |
| 178 | 4-butylthiocyclohexyl | H | ethyl | allyl | H | |
| 179 | 4-butylthiocyclohexyl | H | ethyl | (E)-2-butenyl | H | |
| 180 | 4-butylthiocyclohexyl | H | ethyl | (E)-3-chloro-2-propenyl | H | |
| 181 | 4-butylthiocyclohexyl | H | propyl | ethyl | H | |
| 182 | 4-butylthiocyclohexyl | H | propyl | allyl | H | |
| 183 | 4-butylthiocyclohexyl | H | propyl | (E)-2-butenyl | H | |
| 184 | 4-butylthiocyclohexyl | H | propyl | (E)-3-chloro-2-propenyl | H | |
| 185 | 4-phenylthiocyclohexyl | H | ethyl | ethyl | H | |
| 186 | 4-phenylthiocyclohexyl | H | ethyl | allyl | H | |
| 187 | 4-phenylthiocyclohexyl | H | ethyl | (E)-2-butenyl | H | |
| 188 | 4-phenylthiocyclohexyl | H | ethyl | (E)-3-chloro-2-propenyl | H | |
| 189 | 4-phenylthiocyclohexyl | H | propyl | ethyl | H | |
| 190 | 4-phenylthiocyclohexyl | H | propyl | allyl | H | |
| 191 | 4-phenylthiocyclohexyl | H | propyl | (E)-2-butenyl | H | |
| 192 | 4-phenylthiocyclohexyl | H | propyl | (E)-3-chloro-2-propenyl | H | |
| 193 | 3-phenylthiocyclohexyl | H | ethyl | ethyl | H | |
| 194 | 3-phenylthiocyclohexyl | H | ethyl | allyl | H | |
| 195 | 3-phenylthiocyclohexyl | H | ethyl | (E)-2-butenyl | H | |
| 196 | 3-phenylthiocyclohexyl | H | ethyl | (E)-3-chloro-2-propenyl | H | |
| 197 | 3-phenylthiocyclohexyl | H | propyl | ethyl | H | |
| 198 | 3-phenylthiocyclohexyl | H | propyl | allyl | H | |
| 199 | 3-phenylthiocyclohexyl | H | propyl | (E)-2-butenyl | H | |
| 200 | 3-phenylthiocyclohexyl | H | propyl | (E)-3-chloro-2-propenyl | H | |

TABLE 1-continued

| Compound no. | R³ | R² | R¹ | R⁴ | Y | ¹H-NMR data |
|---|---|---|---|---|---|---|
| 201 | 4-trimethylsilycyclohexyl | H | ethyl | ethyl | H | |
| 202 | 4-trimethylsilycyclohexyl | H | ethyl | allyl | H | |
| 203 | 4-trimethylsilycyclohexyl | H | ethyl | (E)-2-butenyl | H | |
| 204 | 4-trimethylsilycyclohexyl | H | ethyl | (E)-3-chloro-2-propenyl | H | |
| 205 | 4-trimethylsilycyclohexyl | H | propyl | ethyl | H | |
| 206 | 4-trimethylsilycyclohexyl | H | propyl | allyl | H | |
| 207 | 4-trimethylsilycyclohexyl | H | propyl | (E)-2-butenyl | H | |
| 208 | 4-trimethylsilycyclohexyl | H | propyl | (E)-3-chloro-2-propenyl | H | |
| 209 | 3-trimethylsilycyclohexyl | H | ethyl | ethyl | H | |
| 210 | 3-trimethylsilycyclohexyl | H | ethyl | allyl | H | |
| 211 | 3-trimethylsilycyclohexyl | H | ethyl | (E)-2-butenyl | H | |
| 212 | 3-trimethylsilycyclohexyl | H | ethyl | (E)-3-chloro-2-propenyl | H | |
| 213 | 3-trimethylsilycyclohexyl | H | propyl | ethyl | H | |
| 214 | 3-trimethylsilycyclohexyl | H | propyl | allyl | H | |
| 215 | 3-trimethylsilycyclohexyl | H | propyl | (E)-2-butenyl | H | |
| 216 | 3-trimethylsilycyclohexyl | H | propyl | (E)-3-chloro-2-propenyl | H | |
| 217 | 4-diethylphosphonocyclohexyl | H | ethyl | ethyl | H | |
| 218 | 4-diethylphosphonocyclohexyl | H | ethyl | allyl | H | |
| 219 | 4-diethylphosphonocyclohexyl | H | ethyl | (E)-2-butenyl | H | |
| 220 | 4-diethylphosphonocyclohexyl | H | ethyl | (E)-3-chloro-2-propenyl | H | |
| 221 | 4-diethylphosphonocyclohexyl | H | propyl | ethyl | H | |
| 222 | 4-diethylphosphonocyclohexyl | H | propyl | allyl | H | |
| 223 | 4-diethylphosphonocyclohexyl | H | propyl | (E)-2-butenyl | H | |
| 224 | 4-diethylphosphonocyclohexyl | H | propyl | (E)-3-chloro-2-propenyl | H | |
| 225 | 4-methylsulfonylcyclohexyl | H | ethyl | ethyl | H | |
| 226 | 4-methylsulfonylcyclohexyl | H | ethyl | allyl | H | |
| 227 | 4-methylsulfonylcyclohexyl | H | ethyl | (E)-2-butenyl | H | |
| 228 | 4-methylsulfonylcyclohexyl | H | ethyl | (E)-3-chloro-2-propenyl | H | |
| 229 | 4-methylsulfonylcyclohexyl | H | propyl | ethyl | H | |
| 230 | 4-methylsulfonylcyclohexyl | H | propyl | allyl | H | |
| 231 | 4-methylsulfonylcyclohexyl | H | propyl | (E)-2-butenyl | H | |
| 232 | 4-methylsulfonylcyclohexyl | H | propyl | (E)-3-chloro-2-propenyl | H | |
| 233 | 4-acetoxycyclohexyl | H | ethyl | ethyl | H | |
| 234 | 4-acetoxycyclohexyl | H | ethyl | allyl | H | |
| 235 | 4-acetoxycyclohexyl | H | ethyl | (E)-2-butenyl | H | |
| 236 | 4-acetoxycyclohexyl | H | ethyl | (E)-3-chloro-2-propenyl | H | |
| 237 | 4-acetoxycyclohexyl | H | propyl | ethyl | H | |
| 238 | 4-acetoxycyclohexyl | H | propyl | allyl | H | |
| 239 | 4-acetoxycyclohexyl | H | propyl | (E)-2-butenyl | H | |
| 240 | 4-acetoxycyclohexyl | H | propyl | (E)-3-chloro-2-propenyl | H | |
| 241 | 4-benzoyloxycyclohexyl | H | ethyl | ethyl | H | |
| 242 | 4-benzoyloxycyclohexyl | H | ethyl | allyl | H | |
| 243 | 4-benzoyloxycyclohexyl | H | ethyl | (E)-2-butenyl | H | |
| 244 | 4-benzoyloxycyclohexyl | H | ethyl | (E)-3-chloro-2-propenyl | H | |
| 245 | 4-benzoyloxycyclohexyl | H | propyl | ethyl | H | |
| 246 | 4-benzoyloxycyclohexyl | H | propyl | allyl | H | |
| 247 | 4-benzoyloxycyclohexyl | H | propyl | (E)-2-butenyl | H | |
| 248 | 4-benzoyloxycyclohexyl | H | propyl | (E)-3-chloro-2-propenyl | H | |
| 249 | 4-hydroxycyclohexyl | H | ethyl | ethyl | H | |
| 250 | 4-hydroxycyclohexyl | H | ethyl | allyl | H | |
| 251 | 4-hydroxycyclohexyl | H | ethyl | (E)-2-butenyl | H | |
| 252 | 4-hydroxycyclohexyl | H | ethyl | (E)-3-chloro-2-propenyl | H | |
| 253 | 4-hydroxycyclohexyl | H | propyl | ethyl | H | |
| 254 | 4-hydroxycyclohexyl | H | propyl | allyl | H | |
| 255 | 4-hydroxycyclohexyl | H | propyl | (E)-2-butenyl | H | |
| 256 | 4-hydroxycyclohexyl | H | propyl | (E)-3-chloro-2-propenyl | H | |
| 257 | 4-acetylaminocyclohexyl | H | ethyl | ethyl | H | |
| 258 | 4-acetylaminocyclohexyl | H | ethyl | allyl | H | |
| 259 | 4-acetylaminocyclohexyl | H | ethyl | (E)-2-butenyl | H | |
| 260 | 4-acetylaminocyclohexyl | H | ethyl | (E)-3-chloro-2-propenyl | H | |
| 261 | 4-acetylaminocyclohexyl | H | propyl | ethyl | H | |
| 262 | 4-acetylaminocyclohexyl | H | propyl | allyl | H | |
| 263 | 4-acetylaminocyclohexyl | H | propyl | (E)-2-butenyl | H | |
| 264 | 4-acetylaminocyclohexyl | H | propyl | (E)-3-chloro-2-propenyl | H | |
| 265 | 4-cyclopropylcarbonylamino-cyclohexyl | H | ethyl | ethyl | H | |
| 266 | 4-cyclopropylcarbonylamino-cyclohexyl | H | ethyl | allyl | H | |
| 267 | 4-cyclopropylcarbonylamino-cyclohexyl | H | ethyl | (E)-2-butenyl | H | |
| 268 | 4-cyclopropylcarbonylamino-cyclohexyl | H | ethyl | (E)-3-chloro-2-propenyl | H | |
| 269 | 4-cyclopropylcarbonylamino-cyclohexyl | H | propyl | ethyl | H | |
| 270 | 4-cyclopropylcarbonylamino-cyclohexyl | H | propyl | allyl | H | |
| 271 | 4-cyclopropylcarbonylamino-cyclohexyl | H | propyl | (E)-2-butenyl | H | |
| 272 | 4-cyclopropylcarbonylamino-cyclohexyl | H | propyl | (E)-3-chloro-2-propenyl | H | |

TABLE 1-continued

| Compound no. | R³ | R² | R¹ | R⁴ | Y | ¹H-NMR data |
|---|---|---|---|---|---|---|
| 273 | 4-carboxycyclohexyl | H | ethyl | ethyl | H | |
| 274 | 4-carboxycyclohexyl | H | ethyl | allyl | H | |
| 275 | 4-carboxycyclohexyl | H | ethyl | (E)-2-butenyl | H | |
| 276 | 4-carboxycyclohexyl | H | ethyl | (E)-3-chloro-2-propenyl | H | |
| 277 | 4-carboxycyclohexyl | H | propyl | ethyl | H | |
| 278 | 4-carboxycyclohexyl | H | propyl | allyl | H | |
| 279 | 4-carboxycyclohexyl | H | propyl | (E)-2-butenyl | H | |
| 280 | 4-carboxycyclohexyl | H | propyl | (E)-3-chloro-2-propenyl | H | |
| 281 | 4-methoxycarbonylcyclohexyl | H | ethyl | ethyl | H | |
| 282 | 4-methoxycarbonylcyclohexyl | H | ethyl | allyl | H | |
| 283 | 4-methoxycarbonylcyclohexyl | H | ethyl | (E)-2-butenyl | H | |
| 284 | 4-methoxycarbonylcyclohexyl | H | ethyl | (E)-3-chloro-2-propenyl | H | |
| 285 | 4-methoxycarbonylcyclohexyl | H | propyl | ethyl | H | |
| 286 | 4-methoxycarbonylcyclohexyl | H | propyl | allyl | H | |
| 287 | 4-methoxycarbonylcyclohexyl | H | propyl | (E)-2-butenyl | H | |
| 288 | 4-methoxycarbonylcyclohexyl | H | propyl | (E)-3-chloro-2-propenyl | H | |
| 289 | 4-methylcarbamoylcyclohexyl | H | ethyl | ethyl | H | |
| 290 | 4-methylcarbamoylcyclohexyl | H | ethyl | allyl | H | |
| 291 | 4-methylcarbamoylcyclohexyl | H | ethyl | (E)-2-butenyl | H | |
| 292 | 4-methylcarbamoylcyclohexyl | H | ethyl | (E)-3-chloro-2-propenyl | H | |
| 293 | 4-methylcarbamoylcyclohexyl | H | propyl | ethyl | H | |
| 294 | 4-methylcarbamoylcyclohexyl | H | propyl | allyl | H | |
| 295 | 4-methylcarbamoylcyclohexyl | H | propyl | (E)-2-butenyl | H | |
| 296 | 4-methylcarbamoylcyclohexyl | H | propyl | (E)-3-chloro-2-propenyl | H | |
| 297 | 4-(1,3-dioxolan-2-yl)-cyclohexyl | H | ethyl | ethyl | H | |
| 298 | 4-(1,3-dioxolan-2-yl)-cyclohexyl | H | ethyl | allyl | H | |
| 299 | 4-(1,3-dioxolan-2-yl)-cyclohexyl | H | ethyl | (E)-2-butenyl | H | |
| 300 | 4-(1,3-dioxolan-2-yl)-cyclohexyl | H | ethyl | (E)-3-chloro-2-propenyl | H | |
| 301 | 4-(1,3-dioxolan-2-yl)-cyclohexyl | H | propyl | ethyl | H | |
| 302 | 4-(1,3-dioxolan-2-yl)-cyclohexyl | H | propyl | allyl | H | |
| 303 | 4-(1,3-dioxolan-2-yl)-cyclohexyl | H | propyl | (E)-2-butenyl | H | |
| 304 | 4-(1,3-dioxolan-2-yl)-cyclohexyl | H | propyl | (E)-3-chloro-2-propenyl | H | |
| 305 | 4-dimethoxymethylcyclohexyl | H | ethyl | ethyl | H | |
| 306 | 4-dimethoxymethylcyclohexyl | H | ethyl | allyl | H | |
| 307 | 4-dimethoxymethylcyclohexyl | H | ethyl | (E)-2-butenyl | H | |
| 308 | 4-dimethoxymethylcyclohexyl | H | ethyl | (E)-3-chloro-2-propenyl | H | |
| 309 | 4-dimethoxymethylcyclohexyl | H | propyl | ethyl | H | |
| 310 | 4-dimethoxymethylcyclohexyl | H | propyl | allyl | H | |
| 311 | 4-dimethoxymethylcyclohexyl | H | propyl | (E)-2-butenyl | H | |
| 312 | 4-dimethoxymethylcyclohexyl | H | propyl | (E)-3-chloro-2-propenyl | H | |
| 313 | 2-methoxymethyl-5-methyl-cyclohexyl | H | ethyl | ethyl | H | |
| 314 | 2-methoxymethyl-5-methyl-cyclohexyl | H | ethyl | allyl | H | |
| 315 | 2-methoxymethyl-5-methyl-cyclohexyl | H | ethyl | (E)-2-butenyl | H | |
| 316 | 2-methoxymethyl-5-methyl-cyclohexyl | H | ethyl | (E)-3-chloro-2-propenyl | H | |
| 317 | 2-methoxymethyl-5-methyl-cyclohexyl | H | propyl | ethyl | H | |
| 318 | 2-methoxymethyl-5-methyl-cyclohexyl | H | propyl | allyl | H | |
| 319 | 2-methoxymethyl-5-methyl-cyclohexyl | H | propyl | (E)-2-butenyl | H | |
| 320 | 2-methoxymethyl-5-methyl-cyclohexyl | H | propyl | (E)-3-chloro-2-propenyl | H | |
| 321 | 5-methoxymethyl-2-methyl-cyclohexyl | H | ethyl | ethyl | H | |
| 322 | 5-methoxymethyl-2-methyl-cyclohexyl | H | ethyl | allyl | H | |
| 323 | 5-methoxymethyl-2-methyl-cyclohexyl | H | ethyl | (E)-2-butenyl | H | |
| 324 | 5-methoxymethyl-2-methyl-cyclohexyl | H | ethyl | (E)-3-chloro-2-propenyl | H | |
| 325 | 5-methoxymethyl-2-methyl-cyclohexyl | H | propyl | ethyl | H | |
| 326 | 5-methoxymethyl-2-methyl-cyclohexyl | H | propyl | allyl | H | |
| 327 | 5-methoxymethyl-2-methyl-cyclohexyl | H | propyl | (E)-2-butenyl | H | |
| 328 | 5-methoxymethyl-2-methyl-cyclohexyl | H | propyl | (E)-3-chloro-2-propenyl | H | |

TABLE 1-continued

| Compound no. | R³ | R² | R¹ | R⁴ | Y | ¹H-NMR data |
|---|---|---|---|---|---|---|
| 329 | 3-ethylthio-4-hydroxy-4--methylcyclohexyl | H | ethyl | ethyl | H | |
| 330 | 3-ethylthio-4-hydroxy-4--methylcyclohexyl | H | ethyl | allyl | H | 1.34(s), 4.51(d), 6.0(m) |
| 331 | 3-ethylthio-4-hydroxy-4--methylcyclohexyl | H | ethyl | (E)-2-butenyl | H | 1.15(t), 1.36(s), 4.45(d) |
| 332 | 3-ethylthio-4-hydroxy-4--methylcyclohexyl | H | ethyl | (E)-3-chloro-2-propenyl | H | 1.35(s), 4.54(d), 6.37(d) |
| 333 | 3-ethylthio-4-hydroxy-4--methylcyclohexyl | H | propyl | ethyl | H | 0.98(t), 4.12(q) |
| 334 | 3-ethylthio-4-hydroxy-4--methylcyclohexyl | H | propyl | allyl | H | 0.97(t), 1.38(s), 4.56(d) |
| 335 | 3-ethylthio-4-hydroxy-4--methylcyclohexyl | H | propyl | (E)-2-butenyl | H | |
| 336 | 3-ethylthio-4-hydroxy-4--methylcyclohexyl | H | propyl | (E)-3-chloro-2-propenyl | H | 0.95(t), 1.34(s), 4.52(d) |
| 337 | 2-methoxymethyl-5-methyl--3-cyclohexenyl | H | ethyl | ethyl | H | |
| 338 | 2-methoxymethyl-5-methyl--3-cyclohexenyl | H | ethyl | allyl | H | |
| 339 | 2-methoxymethyl-5-methyl--3-cyclohexenyl | H | ethyl | (E)-2-butenyl | H | |
| 340 | 2-methoxymethyl-5-methyl--3-cyclohexenyl | H | ethyl | (E)-3-chloro-2-propenyl | H | |
| 341 | 2-methoxymethyl-5-methyl--3-cyclohexenyl | H | propyl | ethyl | H | |
| 342 | 2-methoxymethyl-5-methyl--3-cyclohexenyl | H | propyl | allyl | H | |
| 343 | 2-methoxymethyl-5-methyl--3-cyclohexenyl | H | propyl | (E)-2-butenyl | H | |
| 344 | 2-methoxymethyl-5-methyl--3-cyclohexenyl | H | propyl | (E)-3-chloro-2-propenyl | H | |
| 345 | 5-methoxymethyl-2-methyl-3--cyclohexenyl | H | ethyl | ethyl | H | |
| 346 | 5-methoxymethyl-2-methyl-3--cyclohexenyl | H | ethyl | allyl | H | |
| 347 | 5-methoxymethyl-2-methyl-3--cyclohexenyl | H | ethyl | (E)-2-butenyl | H | |
| 348 | 5-methoxymethyl-2-methyl-3--cyclohexenyl | H | ethyl | (E)-3-chloro-2-propenyl | H | |
| 349 | 5-methoxymethyl-2-methyl-3--cyclohexenyl | H | propyl | ethyl | H | |
| 350 | 5-methoxymethyl-2-methyl-3--cyclohexenyl | H | propyl | allyl | H | |
| 351 | 5-methoxymethyl-2-methyl-3--cyclohexenyl | H | propyl | (E)-2-butenyl | H | |
| 352 | 5-methoxymethyl-2-methyl-3-cyclohexenyl | H | propyl | (E)-3-chloro-2-propenyl | H | |
| 353 | 4,5-dihydroxycyclooctyl | H | ethyl | ethyl | H | |
| 354 | 4,5-dihydroxycyclooctyl | H | ethyl | allyl | H | |
| 355 | 4,5-dihydroxycyclooctyl | H | ethyl | (E)-2-butenyl | H | |
| 356 | 4,5-dihydroxycyclooctyl | H | ethyl | (E)-3-chloro-2-propenyl | H | |
| 357 | 4,5-dihydroxycyclooctyl | H | propyl | ethyl | H | |
| 358 | 4,5-dihydroxycyclooctyl | H | propyl | allyl | H | |
| 359 | 4,5-dihydroxycyclooctyl | H | propyl | (E)-2-butenyl | H | |
| 360 | 4,5-dihydroxycyclooctyl | H | propyl | (E)-3-chloro-2-propenyl | H | |
| 361 | 4,5-diacetoxycyclooctyl | H | ethyl | ethyl | H | |
| 362 | 4,5-diacetoxycyclooctyl | H | ethyl | allyl | H | |
| 363 | 4,5-diacetoxycyclooctyl | H | ethyl | (E)-2-butenyl | H | |
| 364 | 4,5-diacetoxycyclooctyl | H | ethyl | (E)-3-chloro-2-propenyl | H | |
| 365 | 4,5-diacetoxycyclooctyl | H | propyl | ethyl | H | |
| 366 | 4,5-diacetoxycyclooctyl | H | propyl | allyl | H | |
| 367 | 4,5-diacetoxycyclooctyl | H | propyl | (E)-2-butenyl | H | |
| 368 | 4,5-diacetoxycyclooctyl | H | propyl | (E)-3-chloro-2-propenyl | H | |
| 369 | 4-carboxymethylthio-cyclohexyl | H | ethyl | ethyl | H | |
| 370 | 4-carboxymethylthio-cyclohexyl | H | ethyl | allyl | H | |
| 371 | 4-carboxymethylthio-cyclohexyl | H | ethyl | (E)-2-butenyl | H | |
| 372 | 4-carboxymethylthio-cyclohexyl | H | ethyl | (E)-3-chloro-2-propenyl | H | |
| 373 | 4-carboxymethylthio-cyclohexyl | H | propyl | ethyl | H | 2.9(t), 3.3(s), 4.1(q) |
| 374 | 4-carboxymethylthio-cyclohexyl | H | propyl | allyl | H | |
| 375 | 4-carboxymethylthio-cyclohexyl | H | propyl | (E)-2-butenyl | H | |
| 376 | 4-carboxymethylthio-cyclohexyl | H | propyl | (E)-3-chloro-2-propenyl | H | |

TABLE 1-continued

| Compound no. | R³ | R² | R¹ | R⁴ | Y | ¹H-NMR data |
|---|---|---|---|---|---|---|
| 377 | 3-ethylthiocyclohexyl | H | propyl | ethyl | H | 1.0(t), 1.15–1.37 (2t), 4.1(q) |
| 408 | 1-methoxymethylcyclohex-1-yl | H | propyl | ethyl | H | 0.98(t), 3.28(s), 4.10(q) |
| 409 | 3,4-bis(n-butoxycarbonyl)-cyclohexyl | H | ethyl | (E)-3-chloro-2-propenyl | H | 1.13(t), 4.53(d), 6.34(d) |
| 410 | 3,4-bis(n-butoxycarbonyl)-cyclohexyl | H | ethyl | ethyl | H | 1.12(t), 2.91(m), 3.32(m) |
| 411 | 3,4-bis(methoxycarbonyl)-cyclohexyl | H | ethyl | ethyl | H | 1.29(t), 3.67(s), 4.13(g) |
| 412 | 3,4-bis(n-butoxycarbonyl)-cyclohexyl | H | propyl | (E)-3-chloro-2-propenyl | H | 0.93(m), 4.50(d), 6.33(d) |
| 413 | 3,4-bis(n-butoxycarbonyl)-cyclohexyl | H | propyl | allyl | H | 3.86(m), 4.08(m), 4.53(d) |
| 414 | 3,4-bis(n-butoxycarbonyl)-cyclohexyl | H | propyl | ethyl | H | 1.30(t), 3.86(m), 4.08(m) |
| 415 | 3-butyryloxy-4-hydroxy-4-methyl-cyclohexyl | H | ethyl | allyl | H | 0.95(t), 1.98(s), 4.52(d) |
| 416 | 3-butyryloxy-4-hydroxy-4-methyl-cyclohexyl | H | ethyl | (E)-2-butenyl) | H | 0.98(t), 1.19(s), 4.46(d) |
| 417 | 3-butyryloxy-4-hydroxy-4-methyl-cyclohexyl | H | ethyl | (E)-3-chloro-2-propenyl | H | 0.96(t), 1.18(s), 4.52(d) |

TABLE 2

The compounds of the formula I given in Table 2 (Z = oxygen) may be prepared similarly to Example A.

| Compound no. | R³ | R² | R¹ | Y | ¹H-NMR data |
|---|---|---|---|---|---|
| 378 | 3,4-dihydroxycyclohexyl | H | propyl | H | 0.97(t), 3.0(t), 3.5–3.75(m) |
| 379 | 3,4-dihydroxycyclohexyl | H | ethyl | H | |
| 380 | 3,4-diacetoxycyclohexyl | H | ethyl | H | |
| 381 | 3-acetoxy-4-hydroxycyclohexyl | H | propyl | H | |
| 382 | 3-acetylaminocyclohexyl | H | propyl | H | |
| 383 | 4-acetylthiocyclohexyl | H | propyl | H | |
| 384 | 4-carboxymethylthio-cyclohexyl | H | propyl | H | 0.97(t), 3.0(t), 3.34(s) |
| 385 | 3-ethylthiocyclohexyl | H | propyl | H | 0.97(t), 1.26(t), 3.02(t) |
| 386 | 1-methoxymethylcyclohex-1-yl | H | propyl | H | |
| 387 | 4-acetylthiocyclohexyl | H | propyl | H | 0.98(t), 2.32(s), 3.0(t) |
| 388 | 3-acetylthio-4-methyl-cyclohexyl | H | propyl | H | 2.36(s), 3.01(t), 3.98(s) |
| 389 | 3,4-diacetoxycyclohexyl | H | ethyl | H | 1.15(t), 2.06(s), 3.05(g) |
| 390 | 3,4-bis(n-methyl-carbamoyloxy)-cyclohexyl | H | propyl | H | 0.98(t), 2.78(s), 2.97(t) |
| 391 | 3,4-bis(n-butoxycarbonyl)-cyclohexyl | H | ethyl | H | 1.14(t), 3.04(q), 4.10(m) |
| 392 | 3,4-bis(methoxycarbonyl)-cyclohexyl | H | ethyl | H | 1.17(t), 3.07(q), 3.73(s) |
| 393 | 3,4-bis(n-butoxycarbonyl)-cyclohexyl | H | propyl | H | 3.02(t), 3.87(m), 4.07(m) |
| 394 | 3,4-bis(methoxycarbonyl)-cyclohexyl | H | propyl | H | 0.98(t), 3.33(m), 3.68(s) |
| 395 | 3,4-bis(carboxyl)-cyclohexyl | H | propyl | H | 0.93(t), 2.98(t), 3.24(m) |
| 396 | 3,4-bis(carboxyl)-cyclohexyl | H | ethyl | H | 1.04(t), 12.10(s), 17.95(s) |
| 397 | 3,4-dihydroxy-4-methyl-cyclohexyl | H | ethyl | H | 1.03(t), 2.98(q), 3.35(s) |
| 398 | 3,4-dihydroxy-4-methyl-cyclohexyl | H | propyl | H | 0.97(t), 3.00(t), 3.66(s) |
| 399 | 3-n-nutyryloxy-4-hydroxy-4-methyl-cyclohexyl | H | ethyl | H | 1.17(s), 2.30(t), 3.05(q) |
| 400 | 3-benzyoyloxy-4-hydroxy-4-methyl-cyclohexyl | H | propyl | H | 1.23(s), 1.42(s), 5.09(s) |
| 401 | 4-hydroxy-4-methyl-3-methylthio-cyclohexyl | H | propyl | H | 0.98(t), 1.19(s), 3.01(t) |
| 402 | 3-ethylthio-4-hydroxy-4-methyl-cyclohexyl | H | ethyl | H | 1.13(t), 1.37(s), 3.04(q) |
| 403 | 3-ethylthio-4-hydroxy-4-methyl-cyclohexyl | H | propyl | H | 0.93(t), 1.18(s), 3.00(t) |
| 404 | 3-acetylthio-4-hydroxy-4-methyl-cyclohexyl | H | propyl | H | 0.98(t), 1.28(s), 3.79(s) |
| 405 | 3-mercapto-4-methyl-cyclohexyl | H | ethyl | H | 1.08(t), 1.13(s), 3.05(q) |
| 406 | 3-acetylthio-4-methyl-cyclohexyl | H | ethyl | H | 2.32(s), 3.05(q), 3.98(s) |

TABLE 2-continued

The compounds of the formula I given in Table 2 (Z = oxygen) may be prepared similarly to Example A.

| Compound no. | R³ | R² | R¹ | Y | ¹H-NMR data |
|---|---|---|---|---|---|
| 407 | 3,4-bis(carboxy)-cyclohexyl | H | propyl | H | 0.93(t), 2.98(t), 3.24(m) |

The compounds of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

The formulations contain from 0.1 to 95, and preferably 0.5 to 90, % by weight of active ingredient.

Examples of formulations are given below.

I. 90 parts by weight of compound no. 5 is mixed with 10 parts by weight of N-methyl-alpha-pyrrolidone. A mixture is obtained which is suitable for application in the form of very fine drops.

II. 20 parts by weight of compound no. 37 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 15 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 7 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 12 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 4 is intimately mixed with 97 parts by weight of particulate kaolin. A dust is obtained containing 3% by weight of the active ingredient.

VII. 30 parts by weight of compound no. 32 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 12 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

IX. 40 parts by weight of compound no. 3 is dissolved in 60 parts by weight of a mixture consisting of 93 wt % xylene and 7 wt % of the adduct of 8 moles of ethylene oxide and 1 mole of nonylphenol. A solution is obtained containing 40 wt % of the active ingredient.

The cyclohexenone derivatives of the formula I in which Z is NOR$^4$ have a good herbicidal action preferably on species from the Gramineae family. They are tolerated by, and are thus selective in, broadleaved crops and monocotyledons not belonging to the Gramineae family. Some of the novel compounds are selective in Gramineae crops such as wheat and rice and also combat unwanted grasses. The active ingredients may be applied pre- or post-emergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the plants to be combated and their growth stage, and varies from 0.025 to 3 kg/ha, but is preferably from 0.05 to 0.5 kg/ha.

The action of cyclohexenone derivatives of the formula I (Z=NOR$^4$) on plant growth is demonstrated in greenhouse experiments.

The vessels employed were plastic flowerpots having a volume of 300 cm$^3$, and which were filled with a sandy loam containing about 3.0% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were first grown in the vessels to a height of from 3 to 15 cm, depending on growth form, before being treated. The soybean plants were grown in a peat-enriched substrate. For this treatment, either plants which had been sown directly in the pots and grown there were selected, or plants which had been grown from seedlings and were transplanted to the pots a few days before treatment. The application rates for postemergence treatment were 0.03 to 0.125 kg of active ingredient per hectare. No covers were placed on the vessels in this method.

The pots were set up in the greenhouse—species from warmer areas at from 20° to 35° C., and species from moderate climates at 10° at 25° C. The experiments were run for 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were Alopecurus myosuroides, Avena fatua, Avena sativa, Digitaria sanguinalis, Echinochloa crus-galli, Glycine max., Lolium multiflorum, Medicago sativa, Setaria italica, Sinapis alba, Sorghum halepense and Zea mays.

On preemergence application of 3 kg/ha of compounds nos. 5, 7, 37, 16, 15, 12 and 9 selected by way of example, plants from the Gramineae family were well combated. Mustard, as an example of a broadleaved crop plant, remained completed uninfluenced.

On postemergence application, for instance compounds nos. 8 and 377 proved suitable for combating unwanted grass growth. The broadleaved crop plant alfalfa exhibited no damage whatsoever.

Compounds nos. 7, 4, 37 and 32, again selected by way of example, exhibited a strong herbicidal action on grasses, whilst soybeans, as a dicotyledonous crop plant, were completely undamaged.

A broad spectrum of grasses in soybeans can be selectively combated with postemergence application of low rates of compounds nos. 12 and 3.

For example compound no. 24 had a strong herbicidal action on unwanted grass species without causing any damage to the growth of the wheat plants.

Unwanted grassy vegetation can be well combated with compounds nos. 71, 70 and 72, for example, without any damage being caused to alfalfa.

In view of the spectrum of weeds which can be combated, the tolerance by crop plants or the desired influence of their growth, and in view of the wide variety of application methods, the compounds according to the invention may be used in a large number of crops, for example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |

| Botanical name | Common name |
| --- | --- |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglan regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N rustica) | tobacco |
| Olea europaea | olive trees |
| Oryza sativa | rice |
| Phaseolus lunatus | limabeans |
| Phaseolus mungo | mungbeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (S. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the cyclohexenone derivatives may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, quinolinecarboxylic acids, etc.

It may also be useful to apply the cyclohexenone derivatives, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexenone derivative of the formula I

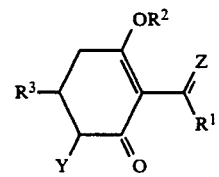

where
$R^1$ is $C_1$-$C_4$-alkyl,
$R^2$ is hydrogen,
$R^3$ is substituted cyclohexyl which contains 0 to 1 methyl groups and 2 substituents selected from the group consisting of hydroxyl, $C_1$-$C_4$-alkylthio, and combinations thereof
Y is hydrogen, methoxycarbonyl, cyano, $C_1$-$C_4$-alkyl or halogen and
Z is oxygen or a radical $NOR_4$ where $R^4$ is $C_1$-$C_4$-alkyl, $C_3$ or $C_4$-alkenyl, $C_3$- or $C_4$-alkynyl, $C_2$-$C_4$-haloalkyl, $C_2$-$C_4$-haloalkenyl, or $C_2$-$C_4$-alkoxyalkyl,
or a salt thereof.

2. A herbicidal composition containing an inert additive and a cyclohexenone derivative of the formula I as set forth in claim 1, Z denoting $NOR^4$.

3. A process for combating unwanted plant growth, wherein the unwanted plants and/or the area to be kept free from unwanted plant growth are treated with a herbicidally effective amount of a cyclohexenone derivative of the formula I as set forth in claim 1, Z denoting $NOR^4$.

4. A composition for regulating plant growth, containing an inert additive and a cyclohexenone derivative of the formula I as set forth in claim 1, Z denoting oxygen.

5. A process for regulating plant growth, wherein a cyclohexenone derivative of the formula I as set forth in claim 1, Z denoting oxygen, is allowed to act on the plants and/or their habitat.

6. 5-(3,4-dihydroxycyclohexyl)-2-[1-(ethoxyimino)-butyl]-3-hydroxy-2-cyclohexen-1-one.

7. 5-(3,4-dihydroxycyclohexyl)-2-[1-(E-3-chloro-2-propenyl-oxyimino)-propyl]-3-hydroxy-2-cyclohexen-1-one.

8. A cyclohexenone derivative as defined in claim 1, wherein $R^3$ is a 3,4-dihydroxycyclohexyl radical of the formula

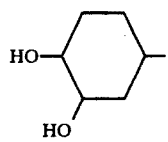
9. A cyclohexenone derivative as defined in claim 1, wherein $R^3$ is a 3-($C_1$-$C_4$-alkylthio)-4-hydroxy-4-methyl cyclohexyl radical of the formula
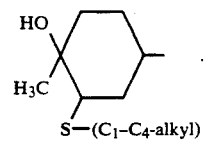
* * * * *